(12) United States Patent
Tumminaro et al.

(10) Patent No.: US 10,226,614 B2
(45) Date of Patent: Mar. 12, 2019

(54) ONE-WAY CHECK VALVE

(75) Inventors: Robert F. Tumminaro, Elk Grove Village, IL (US); Christine A. Fredricks, Mount Prospect, IL (US); Frank K. Villari, Oak Park, IL (US)

(73) Assignee: Illinois Tool Works Inc., Glenview, IL (US)

( * ) Notice: Subject to any disclaimer, the term of this patent is extended or adjusted under 35 U.S.C. 154(b) by 595 days.

(21) Appl. No.: 13/257,298

(22) PCT Filed: Mar. 5, 2010

(86) PCT No.: PCT/US2010/026366
§ 371 (c)(1),
(2), (4) Date: Sep. 17, 2011

(87) PCT Pub. No.: WO2010/107597
PCT Pub. Date: Sep. 23, 2010

(65) Prior Publication Data
US 2012/0004623 A1    Jan. 5, 2012

Related U.S. Application Data

(60) Provisional application No. 61/161,607, filed on Mar. 19, 2009.

(51) Int. Cl.
*A61M 39/24* (2006.01)

(52) U.S. Cl.
CPC ........ *A61M 39/24* (2013.01); *Y10T 137/7879* (2015.04)

(58) Field of Classification Search
CPC .......... A61M 2039/2433; A61M 39/24; A61M 2039/242; A61M 2039/246; A61M 2039/2473

USPC ...... 604/247, 246, 167.02, 167.03, 256, 252
See application file for complete search history.

(56) References Cited

U.S. PATENT DOCUMENTS

| | | | |
|---|---|---|---|
| 3,710,942 A | | 1/1973 | Rosenberg |
| 3,854,907 A | * | 12/1974 | Rising ............................. 96/219 |
| 4,141,379 A | | 2/1979 | Manske |
| 4,468,224 A | * | 8/1984 | Enzmann et al. ............ 604/247 |
| 4,765,372 A | * | 8/1988 | Beecher ................ A61M 39/24 137/843 |
| 6,105,609 A | * | 8/2000 | Polidan et al. ............ 137/515.7 |
| 2005/0159714 A1 | * | 7/2005 | Gibson et al. ........... 604/288.03 |
| 2008/0058720 A1 | | 3/2008 | Spohn et al. |
| 2009/0209917 A1 | * | 8/2009 | Tanaka et al. ................ 604/174 |
| 2009/0292252 A1 | * | 11/2009 | Lareau .................. A61M 39/24 604/167.04 |

FOREIGN PATENT DOCUMENTS

WO        9208503  A2    5/1992

OTHER PUBLICATIONS

ISR for PCT/US2010/026366 dated May 12, 2010.

* cited by examiner

*Primary Examiner* — Lauren P Farrar
(74) *Attorney, Agent, or Firm* — Joseph M. Butscher; The Small Patent Law Group, LLC (57) ABSTRACT

A one-way check valve in an IV system set is provided with structural features to capture contaminant particles and inhibit the particles from adversely impacting the performance of the check valve. A screen can be provided upstream of the valve seat and the valve may be provided with flow channels for accumulating the particles. Modifications of the valve seat provide open volumes for accumulating contaminants.

20 Claims, 6 Drawing Sheets

ONE-WAY CHECK VALVE

CROSS-REFERENCE TO RELATED APPLICATIONS

The present application is national phase of PCT/US2010/026366 filed Mar. 5, 2011 and claims the benefits of U.S. Provisional Application Ser. No. 61/161,607 filed Mar. 19, 2009.

FIELD OF THE INVENTION

The present invention relates generally to one-way check valves, and more particularly, to one-way check valves used in medical fluid delivery systems; and, still more particularly, to contaminant screens and particulate isolating features to protect check valve performance in intravenous (IV) administration sets.

BACKGROUND OF THE INVENTION

It is known to provide intravenous (IV) drug and fluid delivery systems that include a primary line connected to a bag of saline or other fluids, and a branch or auxiliary line connectable to supplies of drugs or other treatment fluids. The branch line and main line are connected at a Y-connector. A check valve is provided in the main line to prevent back flow of the secondary fluid into the main fluid bag. When a drug is dispensed, the back flow pressure on the check valve closes the valve to prevent back flow of the drug into the saline or other non-drug bag. When a drug or other fluid is not dispensed from the auxiliary line, saline flows freely through the check valve.

A known check valve for this purpose is taught by U.S. Pat. No. 4,765,372. The valve disclosed therein includes a housing, a biasable diaphragm within the housing and a valve seat carried by the housing against which the diaphragm is urgeable. The housing has a fluid inlet and a fluid outlet. The diaphragm is preferably disposed transverse to a preselected direction of fluid flow through the housing for controlling fluid flow therethrough. The diaphragm can be urged against the seat for preventing fluid from flowing contrary to the preselected direction of flow. The housing engages opposite sides of the diaphragm so that areas of the diaphragm can be moved away from and toward the valve seat without the diaphragm being displaced from its operative position within the valve.

While valves of the type described have worked successfully, contaminants in the system can interfere with proper operation. If a contaminant particle embeds itself in the diaphragm or seal surface, a proper seal may not be provided. The particle may prop open the diaphragm, in which case a drug dispensed from the secondary path may back flow through the check valve, thereby preventing the patient from receiving the proper drug dosage concentration or timely delivery of the drug.

Contaminants can be created during the manufacture and assembly of IV sets. Particles from many sources can migrate and be trapped in the IV set, and later be carried by fluids into the check valve. The sources of contaminant particles include and are byproducts of handling, processing and migration of other materials that work their way into the IV set system. For example, it is known to cut tubes and assemble bag spike components to enable attachment to associated devices. Cutting or puncturing the tube can generate tubing debris that can compromise the sealing function if the particles migrate to the check valve. Other particles from the environment also can be trapped in the IV set and be carried to the check valve.

Accordingly, it is desirable and advantageous to protect the sealing area of an IV check valve from contaminant particles that may be part of the fluid flow stream in an IV administering system.

SUMMARY OF THE INVENTION

The present invention provides a screen in a check valve and internal structural features to trap contaminant particles away from the sealing area in the check valve.

In one aspect of one form thereof the present invention provides an IV check valve for IV set systems having a main fluid system and an auxiliary fluid system. The IV check valve has a body with a cavity therein in flow communication with an inlet conduit member and an outlet conduit member. The inlet and outlet conduit members are configured for connecting to IV tubes. A valve seat is provided in the body, with a diaphragm responsive to fluid flow through the body. The diaphragm is spaced from the valve seat along at least a portion thereof for fluid flow from the inlet to the outlet and is fluidly sealed against the valve seat for fluid flow from the outlet to the inlet. A screen is disposed in the body between the inlet and the valve seat In another aspect of another form thereof, the present invention provides a fluid system with a main fluid subsystem including a main fluid source and a main fluid line from the main fluid source connected to a supply line. An auxiliary fluid subsystem includes an auxiliary fluid source and an auxiliary fluid line from the auxiliary fluid source connected to the supply line. A check valve in the main fluid line includes an openable and closable seal including a valve seat and a flexible diaphragm. Contaminant particle capturing structure is provided for isolating contaminant particles away from the seal area or surface.

In a further aspect of a further form thereof, the present invention provides a check valve with a cover having a cover conduit member and a housing connected to the cover. The housing defines a cavity therein and has a housing conduit member. The housing has first and second shoulders therein. The first shoulder is nearer than the second shoulder to the cover. The first shoulder defines a valve seal area. A diaphragm responsive to fluid flow through the valve engages the valve seal area when fluid flows from the cover toward the housing. A particle screen is disposed on the second shoulder.

An advantage of an embodiment of the check valve, in a form thereof, is providing a screen as a component of the check valve, thereby simplifying user application of an IV set having the check valve.

Other features and advantages of the invention will become apparent to those skilled in the art upon review of the following detailed description, claims and drawings in which like numerals are used to designate like features.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting. The use herein of "including", "comprising" and variations thereof is meant to encompass the items listed thereafter and equivalents thereof, as well as additional items and equivalents thereof.

DETAILED DESCRIPTION OF THE PREFERRED EMBODIMENT

Figure 1:
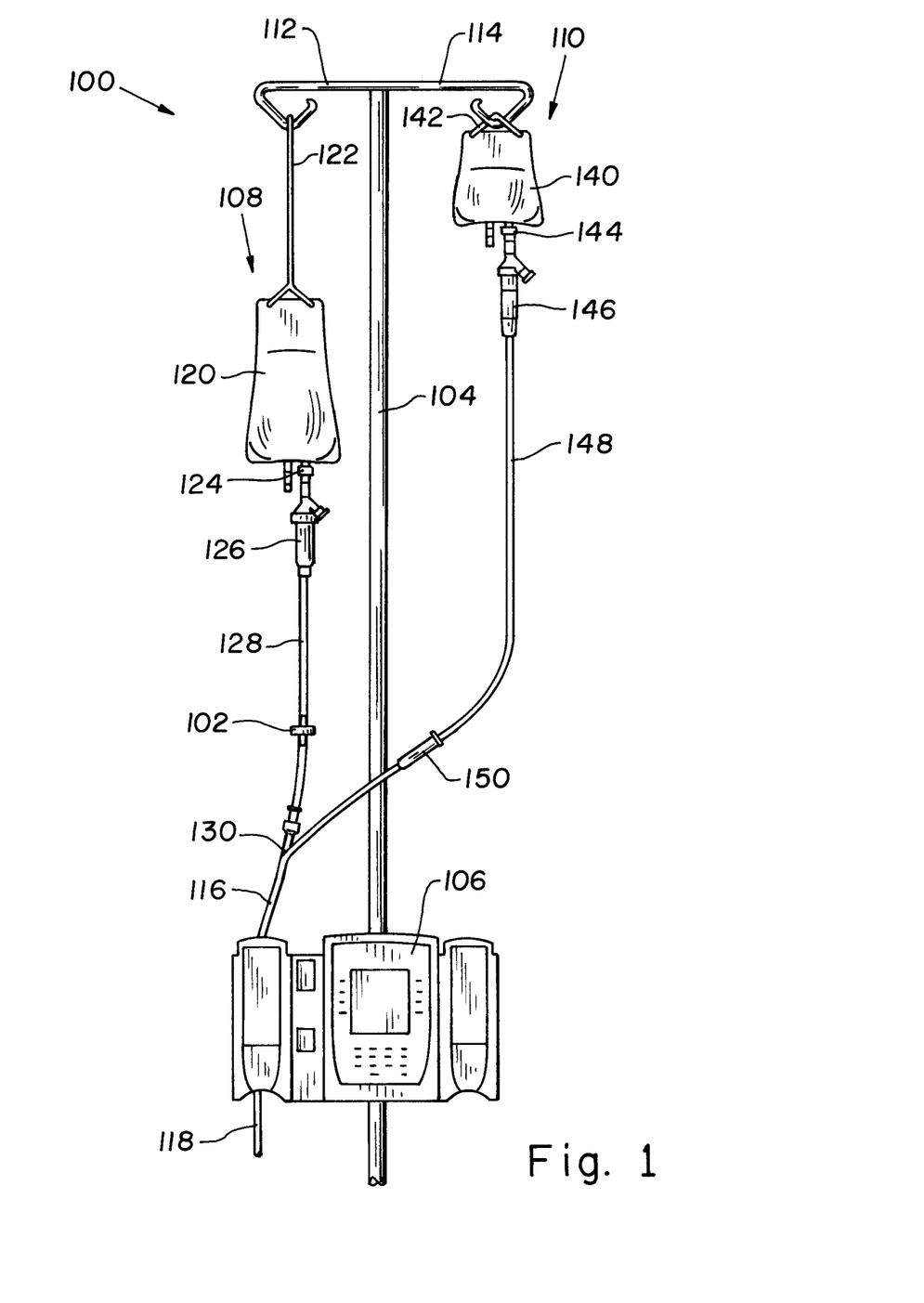
FIG. 1 is a fragmentary perspective view of an IV set having a check valve therein.

Referring now more particularly to the drawings and to FIG. 1 in particular, an IV set system 100 is shown and includes an IV check valve 102 therein. IV set system 100 includes an IV standard or pole 104 carrying an IV pump 106 thereon for administering fluid flow from a main fluid subsystem 108 and a branch or auxiliary fluid subsystem 110. IV standard or pole 104 includes first and second arms 112, 114 from which main fluid subsystem 108 and auxiliary fluid subsystem 110 are suspended. IV pump 106 receives fluid from main fluid subsystem 108 and branch or auxiliary fluid subsystem 110 via a supply line 116 and controls and dispenses the fluids therefrom to the patient via a patient IV line 118.

Main fluid subsystem 108 includes a main fluid source such as a fluid bag 120 which may include or contain saline solution or other fluid to be administered to the patient. Fluid bag 120 is suspended from arm 112 by a tether or strap 122. An outlet feature 124 from fluid bag 120 is connected to a drip chamber 126. A fluid line 128 carries flow from drip chamber 126 to a Y-connector 130. Check valve 102 is disposed in fluid line 128 upstream from Y-connector 130 and enables flow from fluid bag 120 to IV pump 106 while preventing backflow of fluid from auxiliary fluid subsystem toward fluid bag 120.

Branch or auxiliary fluid subsystem 110 includes an auxiliary fluid source such as a fluid bag 140 which may contain drugs or other fluid to be supplied to the patient for treatment. Fluid bag 140 is suspended from arm 114 by a tether or strap 142. An outlet feature 144 from fluid bag 140 is connected to a drip chamber 146. An auxiliary fluid line 148 carries flow from drip chamber 146 to Y-connector 130. A flow regulator 150 can be used in fluid line 148 to control the rate of flow from the fluid bag 130 to IV pump 106.

It should be understood that, apart from check valve 102 to be described in further detail hereinafter, the exemplary IV set system 100 components shown and described are merely exemplary in nature, and check valve 102 can be used in other types of IV systems as well as in fluid flow systems of other types, for other purposes.

Figure 2:
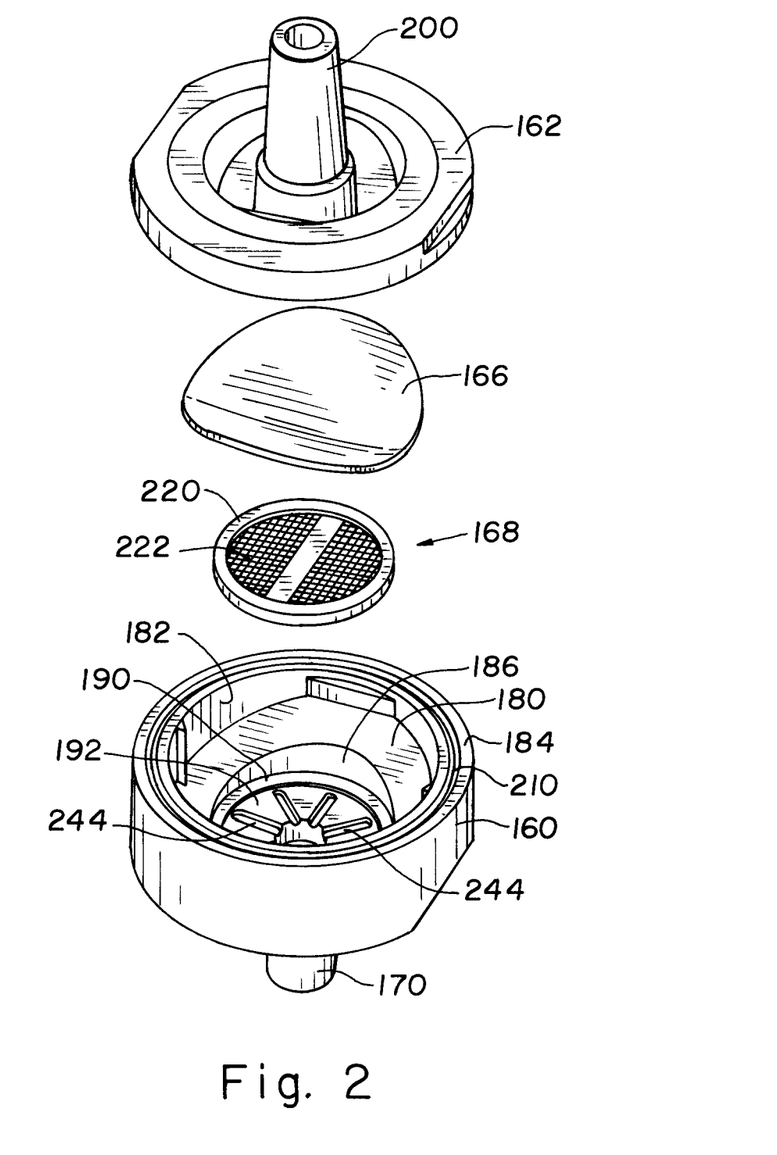
FIG. 2 is an exploded view of a check valve.
Figure 3:
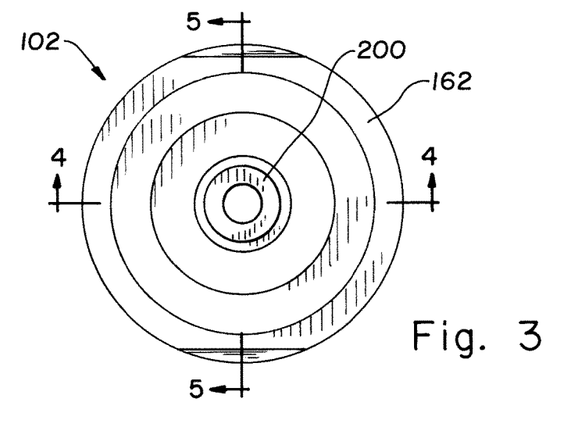
FIG. 3 is a plan view of the check valve.

Check valve 102 has a primary body structure including a housing 160 and a cover 162 that may be attached to one another by an ultrasonic weld joint 164 formed between mating surfaces of the housing and cover. A diaphragm 166 and a screen 168 are provided within housing 160. As shown and described hereinafter, housing 160 defines the inlet structure of the check valve, and cover 162 defines the outlet structure of the check valve with respect to the free flow direction of fluid through the check valve. Accordingly, the check valve is open to flow from housing 160 through cover 162 and closes when backflow occurs from cover 162 toward housing 160. Within IV set system 100, housing 160 is installed toward main fluid bag 120 and cover 162 is installed toward IV pump 106 to allow flow from main fluid bag 120 toward IV pump 106 while closing and eliminating backflow toward main fluid bag 120.

Figures 4, 5:
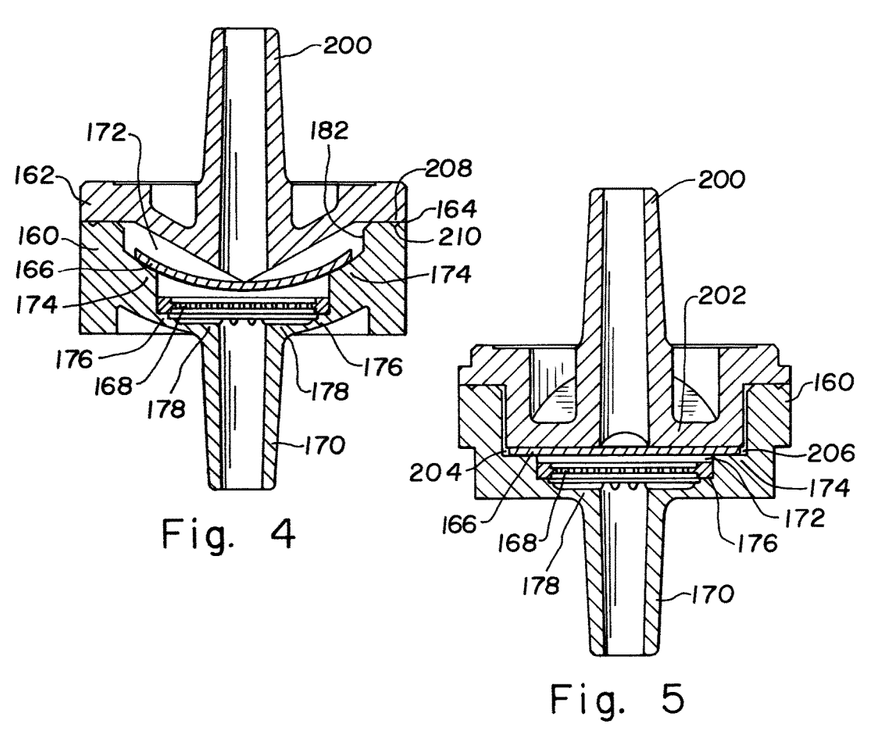
FIG. 4 is a cross-sectional view of the check valve shown in FIG. 3, taken along line 4-4 of FIG. 3.
FIG. 5 is a cross-sectional view of the check valve shown in FIG. 3, taken along line 5-5 of FIG. 3.
Figures 6, 7, 8:
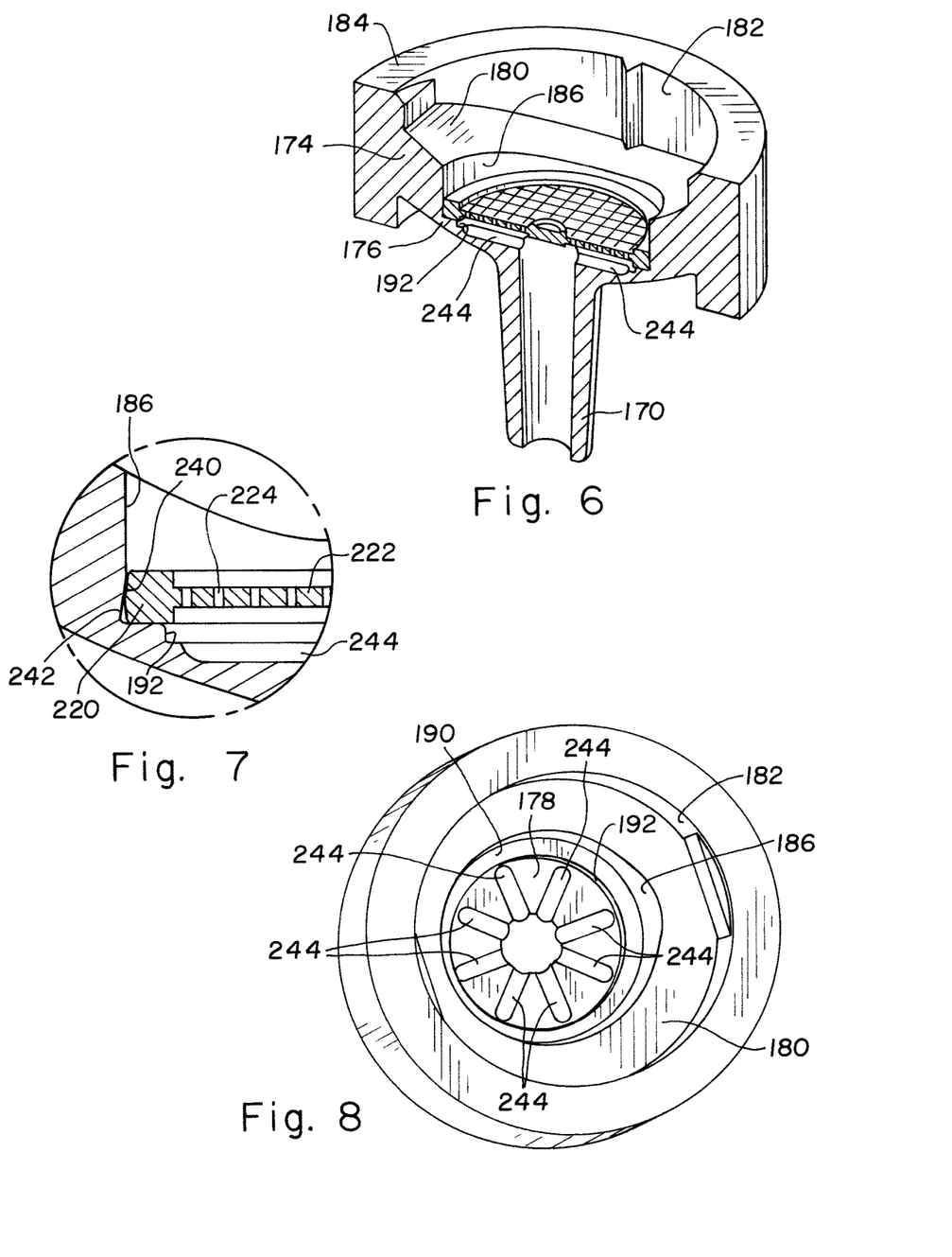
FIG. 6 is an enlarged cutaway view of the check valve.
FIG. 7 is a further enlarged cross-sectional view of a portion of the check valve.
FIG. 8 is a perspective view of a housing of the check valve.

Housing 160 is a cup-like member having an axially disposed integral conduit member 170 through which fluid flows during use. Conduit member 170 may be tapered toward a distal end thereof for receiving IV tubing thereon. Housing 160 defines a cavity 172 therein in fluid flow communication with integral conduit member 170. Cavity 172 defines two levels, having a radially outer shoulder 174 nearer to cover 162 and a radially inner shoulder 176 nearer a bottom or floor 178 of cavity 172.

Shoulder 174 defines a valve seat 180 for operation with diaphragm 166 to provide a valve seal to open and close the valve to fluid flow therethrough. Diaphragm 166 is a curved surface such as a cylindrical section. A radially outer cavity wall 182 extends between an outer edge 184 of housing 160 and shoulder 174 defining valve seat 180. Shoulder 174 further defines a radially inner cavity wall 186 extending from valve seat 180 to radially inner shoulder 176.

Radially inner shoulder 176 defines an inwardly projecting ledge 190 for supporting screen 168. A short bottom cavity wall 192 extends between ledge 190 and bottom or floor 178.

Cover 162 forms a fluid tight seal with housing 160 and has an axially disposed integral conduit member 200 through which fluid flows during use. Conduit member 200 may be tapered toward a distal end thereof for receiving IV tubing thereon. Cover 162 defines an inwardly projecting, generally triangular blade 202 disposed substantially along a diameter of the generally circular cover. Blade 202 projects into cavity 172 and, in the assembled valve, blade 202 pinches diaphragm 166 against valve seat 180 at relatively narrow pinch locations 204, 206 on opposite sides of the valve seat. Clamping pressure against diaphragm 166 between valve seat 180 and blade 202 need only be sufficient to inhibit movement of diaphragm 166 from its operative position. To promote a fluid tight seal and positive location of cover 162 relative to housing 160, a tapered angular projection 208 is provided on cover 162 which is received in a V-shaped groove 210 in outer edge 184 of housing 160.

Diaphragm 166 is flexible, resilient and impervious to the fluids to be handled through the check valve. Diaphragm 166 is sized and shaped to fit within the area defined by radially outer cavity wall 182 while overlapping shoulder 174, and specifically valve seat 180. The substantially half-circle peripheral edges of diaphragm 166 between pinch locations 204, 206 at which blade 202 holds diaphragm 166 against seat 180 are free to move under the influence of fluid flow through the check valve. Accordingly, depending on the direction of fluid flow through the check valve, fluid flow can urge the free peripheral edges of diaphragm 166 away from sealing engagement against valve seat 180, or can urge the diaphragm against the valve seat, depending on the direction of flow.

Screen 168 is a barrier device to inhibit particle passage there past, and includes a frame 220 and a mesh 222 having openings 224 therein. Frame 220 and mesh 222 together may from a single monolithic body. Mesh 222 can be formed in various ways, with differing size openings 224 therethrough. The size of openings 224 is selected to achieve the desired performance with respect to the size of particles to be segregated by the screen. Various processes can be used to manufacture a screen with a desired opening size. For example, screen openings of between about 15µ and 130µ are available by various molding techniques including insert molding and straight molding. Sintered screens are also available. The screens can be made in various grades of synthetic materials such as polyethylene, polyester, polypropylene and the like; and when used for IV applications will be of medical grade materials.

Figure 14:
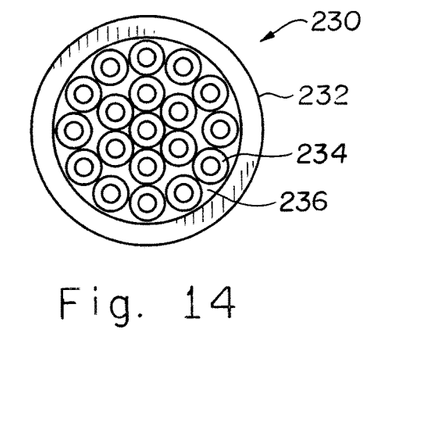
FIG. 14 is a plan view of another embodiment of a screen for the check valve.

While molded screens have been shown and described herein, it should be understood that screens made in other ways and other types of barrier devices can be used. For example, filter media or pervious membranes can be used to prevent particle passage while permitting fluid flow therethrough. Perforated structures including perforated medical grade metals can be used. Laser drilling or other perforating techniques can be used to manufacture the perforated structures. Small bore lumen extrusions can be made of elastomeric or rigid tubing with thin walls, and can be grouped and secured within a matrix field of adhesive or other filler in an outer sheath for slicing to form a screen with consistent opening sizes. FIG. 14 illustrates a screen 230 having an outer sheath 232 and a bundle of hollow tubes 234 held in a matrix 236 within the sheath. Various woven structures and/or nonwoven structures such as needled scrims also can be used to provide the desired barrier against particle passage. Materials incorporating anti-microbial characteristics can be used, either through compounding with anti-microbial or antibacterial agents or by over-coating surfaces with such agents. For example, various silver complex compounds can inhibit bacterial growth on the compound surface. Similar techniques can be used to provide anti-clotting or other characteristics on the surfaces exposed to fluid flow, and particularly on the screen surfaces. For example, injecting heparin into the material can reduce clotting of blood components passing through the check valve.

The exemplary embodiments are shown to be of substantially round shape. However, it should be understood that other shapes and configurations also can be used. For example square or rectangular structures can be used with direct or tretorous paths. So-called dog bone shaped entrance paths can be used, The screen can be retained in housing 160 by means of an interference-fit or snap-fit connection to the housing. For example, as shown in the enlarged view of FIG. 7, outer frame 220 includes an outer edge surface 240 outwardly curved to cooperate with an undercut 242 provided in radially inner cavity wall 186 above ledge 190. Accordingly, screen 168 snaps into and is retained within housing 160. It should be understood that a variety of configurations can be used for holding the screen in the housing, including multiple discrete or continuous detents and/or dimples on the screen or housing.

Figure 9:
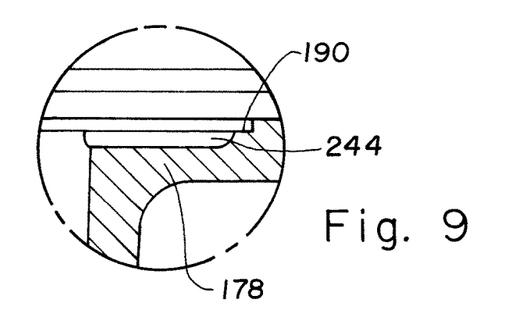
FIG. 9 is an enlarged cross-sectional view of another portion of the check valve.
Figure 10:
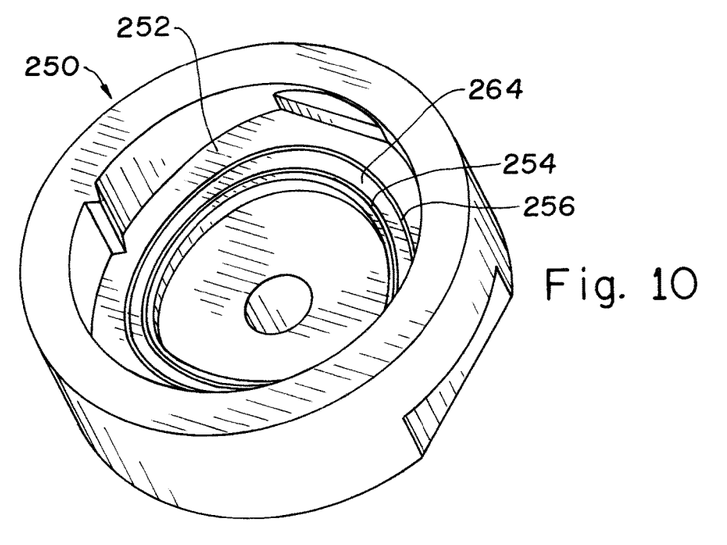
FIG. 10 is an enlarged perspective view of another portion of the check valve.

Other features can be used to protect the seal area from contaminant particles either in conjunction with the particle screen shown or separately from the particle screen. In the exemplary embodiment of check valve 102 a plurality of flow channels 244 are provided in floor 178, which is closely spaced from screen 168. Flow channels 244 can be formed as recesses in floor 178 or can be provided as areas between spaced ridges on the floor. Flow channels 244 increase the gap volume between screen 168 and floor 178 while maintaining a limited overall package size for check valve 102. Flow channels 244 provide increased volume and increased particle holding capacity while limiting flow reduction as particles are accumulated adjacent screen 168. Contaminant particles can accumulate in the flow channels with only limited adverse impact on flow through the screen.

Figure 11:
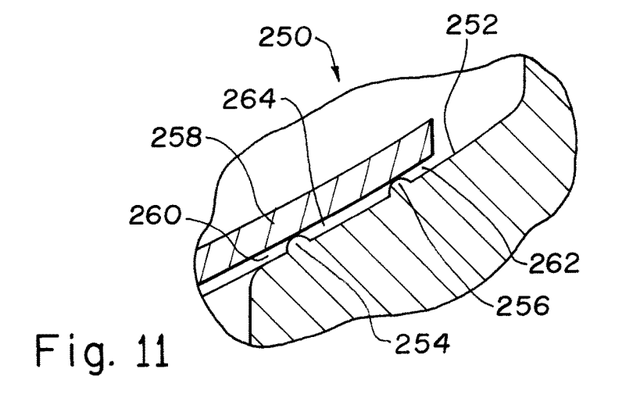
FIG. 11 is an enlarged cross-sectional view of the seal area of the seal in a form of the check valve.

FIGS. 10-13 illustrate further embodiments for a check valve to reduce seal failure resulting from contaminant particles reaching the area of the valve seat. In the exemplary embodiment of a check valve 250, valve seat 252 is provided with continuous valve seat ribs 254, 256. Seal and closure of valve 250 is effected by a diaphragm 258 urged against valve seat ribs 254, 256. As can be seen in FIG. 11, open volumes 260, 262, 264 are provided radially inwardly and radially outwardly of ribs 254, 256 as well as between ribs 254, 256 even when check valve 250 is closed and diaphragm 258 is sealed against valve seat ribs 254, 256. Contaminant particles reaching the area of valve seat 252 and diaphragm 258 can accumulate in the volume spaces 260, 262 or 264 without adversely impacting the seal of diaphragm 258 against valve seat ribs 254, 256.

Figure 12:
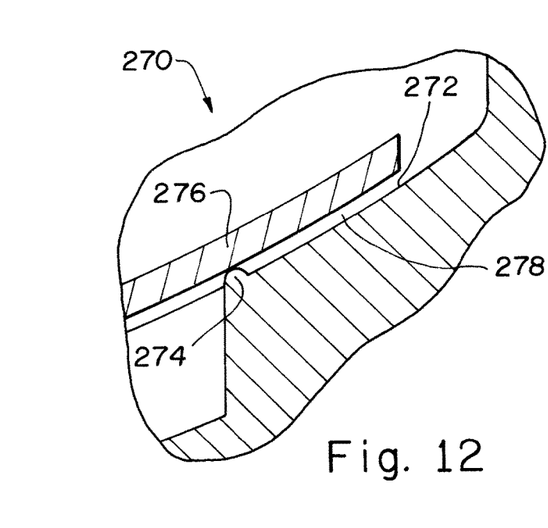
FIG. 12 is an enlarged cross-sectional view of another embodiment of the seal area of the seal.

FIG. 12 illustrates a further embodiment from that shown in FIG. 11. Check valve 270 includes a valve seat 272 having a single continuous valve seat rib 274 and a diaphragm 276 for sealing there against when the valve is closed to flow. An open volume or space 278 is provided radially outwardly of rib 274, between valve seat 272 and diaphragm 276. Accordingly, contaminant particles can accumulate between valve seat 272 and diaphragm 276 within open volume 278 without adversely impacting the seal of diaphragm 276 against valve seat rib 274.

Figure 13:
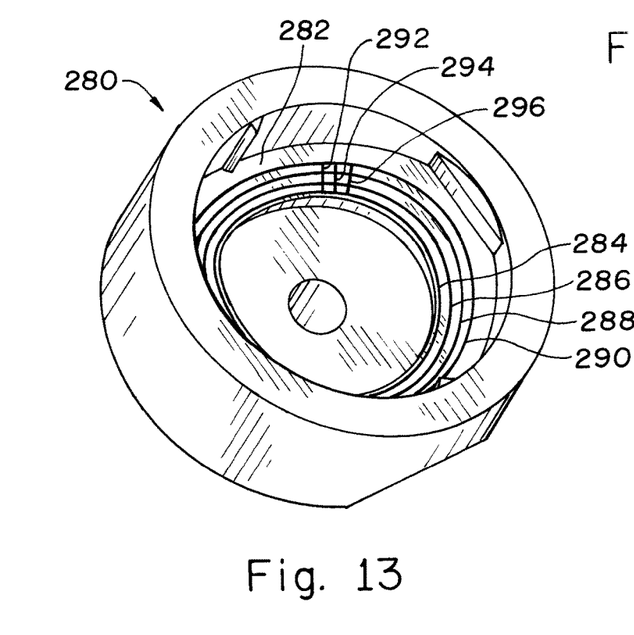
FIG. 13 is a perspective view of another embodiment of the check valve.

FIG. 13 illustrates yet another embodiment of a check valve 280. Valve seat 282 is provided with more than two valve seat ribs, and in the exemplary embodiment shown includes four valve seat ribs 284, 286, 288, 290. Additionally, radial ribs 292, 294, 296 are provided crossing ribs 284, 286, 288, 290. It should be understood that various other types of configurations for ribs on the valve seat can be used to provide an effective seal against a diaphragm while defining open volumes between the ribs, or adjacent a single rib, in which contaminant particles can be accumulated without adversely impacting the effectiveness of the seal created between the diaphragm and the valve seat rib or ribs.

The various features shown and described herein can be used separately or in combination. A screen can be used to prevent larger contaminant particles from reaching the area of the valve seat seal. Flow channels provided in the floor of the check valve adjacent the screen provide areas for accumulating the larger particles without significantly impacting flow through performance of the screen. Small particles not stopped by the screen can be accumulated in the open volume spaces adjacent valve seat ribs without compromising performance of the check valve.

The check valves shown and described herein provide advantages over independent screens or filters provided in tubing lines in that extra assembly efforts are eliminated for users by not having to independently connect a filter within the system. When check valves as described herein are used, particle screening is provided without additional efforts required from the user. Accordingly, inadvertent are intentional omission of an independent screen is eliminated. Further, protection is provided near the seal surface, whereas the effectiveness of an independent screen or filter can be compromised by contaminants entering the system between the independent screen or filter and the check valve. Incorporating the screening function into the check valves resolves this potential disadvantage.

Variations and modifications of the foregoing are within the scope of the present invention. It is understood that the invention disclosed and defined herein extends to all alternative combinations of two or more of the individual features mentioned or evident from the text and/or drawings. All of these different combinations constitute various alternative aspects of the present invention. The embodiments described herein explain the best modes known for practicing the invention and will enable others skilled in the art to utilize the invention. The claims are to be construed to include alternative embodiments to the extent permitted by the prior art.

Various features of the invention are set forth in the following claims.

What is claimed is:

1. An IV check valve for IV set systems having a main fluid system and an auxiliary fluid system, said IV check valve comprising:
    a body including a housing and a cover placed on said housing, said housing having a cavity therein in flow communication with an inlet conduit member and an outlet conduit member, said inlet and said outlet conduit members each being configured for connecting to IV tubes, said cavity further defined by an inner wall having a sidewall and a floor extending from an outer uppermost edge of said housing to said inlet conduit member;
    a valve seat in said body;
    a diaphragm responsive to fluid flow through said body, said diaphragm being spaced from said valve seat along at least a portion thereof for fluid flow from said inlet conduit member to said outlet conduit member and being fluidly sealed against said valve seat for fluid flow from said outlet conduit member to said inlet conduit member, wherein said diaphragm has a circumferential edge extending between top and bottom surfaces with said top and bottom surfaces being curved, non-planar surfaces when fluid flows from said inlet conduit member to said outlet conduit member and when fluid flows from said outlet conduit member to said inlet conduit member;
    at least one recess that inwardly extends into and through at least one portion of an exposed surface of said sidewall and said floor, said at least one portion of said sidewall and said floor extending from an exit of said inlet conduit member to said diaphragm, said at least one recess configured to accumulate contaminant particles; and
    a screen disposed in said body between said inlet and said valve seat.

2. The IV check valve of claim 1, wherein said at least one recess comprises channels into and through said exposed surface of said floor.

3. The IV check valve of claim 2, said valve seat having an elevated valve seat rib, said diaphragm sealingly engaging said rib when said valve is closed.

4. The IV check valve of claim 3, said valve seat having a plurality of elevated valve seat ribs, said diaphragm sealingly engaging said plurality of elevated valve seat ribs when said valve is closed.

5. The IV check valve of claim 1, said valve seat having an elevated valve seat rib, said diaphragm sealingly engaging said rib when said valve is closed.

6. The IV check valve of claim 5, said valve seat having a plurality of elevated valve seat ribs, said diaphragm sealingly engaging said plurality of elevated valve seat ribs when said valve is closed.

7. The IV check valve of claim 5, said valve seat rib being continuous.

8. The IV check valve of claim 1, said screen comprising a bundle of hollow tubes.

9. The IV check valve of claim 1, said screen comprising material with anti-microbial properties.

10. The IV check valve of claim 1, said screen being molded.

11. The IV check valve of claim 1, said screen having a frame and a mesh; a shoulder provided in said cavity; said screen disposed on said shoulder; and said frame being held in said housing by a friction fit.

12. A fluid system comprising:
    a main fluid subsystem including a main fluid source and a main fluid line from said main fluid source connected to a supply line;
    an auxiliary fluid subsystem including an auxiliary fluid source and an auxiliary fluid line from said auxiliary fluid source connected to said supply line; and
    a backflow check valve in said main fluid line, said backflow check valve including, a blade, and an openable and closable seal including a valve seat and a flexible diaphragm having a circumferential edge, wherein said blade pinches said flexible diaphragm against said valve seat at narrow pinch locations near the circumferential edge such that said flexible diaphragm sits against said valve seat until sufficient fluid flow in one direction causes said flexible diaphragm to move away from said valve seat, and wherein said flexible diaphragm is further responsive to fluid flow through said backflow check valve in a second direction which is opposite to the first direction such that said flexible diaphragm seals against said valve seat, said backflow check valve also including contaminant particle capturing structure that inwardly extends into and through an exposed portion of said valve seat for accumulating and isolating contaminant particles away from said seal.

13. The fluid system of claim 12, said check valve having a screen therein.

14. The fluid system of claim 13, said valve seat having a floor, said contaminant particle capturing structure including flow channels inwardly extending into and through the exposed portion of said floor, and said screen overlying said flow channels.

15. The fluid system of claim 12, said valve seat having an elevated valve seat rib, said diaphragm sealingly engaging said valve seat rib when said valve is closed, and a space defined between said diaphragm and said valve seat adjacent said valve seat rib when said diaphragm sealingly engages said valve seat rib.

16. The fluid system of claim 15, said check valve having a screen therein between said main fluid source and said valve seat.

17. The fluid system of claim 15, said valve seat having a plurality of elevated valve seat ribs, said diaphragm sealingly engaging said plurality of elevated valve seat ribs when said valve is closed, and spaces defined between said diaphragm and said valve seat adjacent to and between said ribs when said diaphragm is sealingly engaging said ribs.

18. The IV check valve of claim 1, further comprising:
a cover having a cover conduit member, said cover conduit member including said outlet conduit member;
a housing connected to said cover, said housing including said body and having a housing conduit member, said housing conduit member including said inlet conduit member;
said housing having first and second shoulders therein;
said first shoulder being nearer than said second shoulder to said cover, said first shoulder defining said valve seat; and
said screen disposed on said second shoulder.

19. The check valve of claim 18, said valve seat having a plurality of ribs, said diaphragm engaging said ribs when said valve is closed to flow therethrough, and spaces defined between said diaphragm and said valve seat adjacent said ribs when said valve is closed to flow therethrough.

20. An IV check valve for IV set systems having a main fluid system and an auxiliary fluid system, said IV check valve comprising:
a body including a housing and a cover placed on said housing, said housing having a cavity therein in flow communication with an inlet conduit member and an outlet conduit member, said inlet and said outlet conduit members each being configured for connecting to IV tubes, said cavity further defined by an inner wall having a sidewall and a floor extending from an outer uppermost edge of said housing to said inlet conduit member;

a valve seat in said body;

a diaphragm responsive to fluid flow through said body, said diaphragm being spaced from said valve seat along at least a portion thereof for fluid flow from said inlet conduit member to said outlet conduit member and being fluidly sealed against said valve seat for fluid flow from said outlet conduit member to said inlet conduit member, wherein said diaphragm has a circumferential edge extending between top and bottom surfaces with said top and bottom surfaces being curved, non-planar surfaces when fluid flows from said inlet conduit member to said outlet conduit member and when fluid flows from said outlet conduit member to said inlet conduit member;

a screen disposed in said body between said inlet and said valve seat; and a ledge below said valve seat for retaining said screen, and said floor below said ledge, wherein a plurality of channels are placed in a portion of the floor, said plurality of channels configured to accumulate contaminant particles.

* * * * *